United States Patent [19]

Beckwith

[11] 4,319,875
[45] Mar. 16, 1982

[54] DETACHABLE FASTENER FOR JOINING IMPRESSIONS OF A MOUTH ONTO A DENTAL ARTICULATOR

[76] Inventor: Edward K. Beckwith, 303 La Marina, Santa Barbara, Calif. 93109

[21] Appl. No.: 207,297

[22] Filed: Nov. 17, 1980

[51] Int. Cl.³ .............................................. A61C 11/00
[52] U.S. Cl. .................................................... 433/60
[58] Field of Search ................................. 433/60, 177

[56] References Cited

U.S. PATENT DOCUMENTS 3,510,947  5/1970  Tuccillo ............................... 433/60
4,204,321  5/1980  Scott .................................. 433/177

Primary Examiner—Robert Peshock
Attorney, Agent, or Firm—Daniel J. Meaney, Jr.

[57] ABSTRACT

A detachable fastener for joining impressions of a mouth formed of a lower mouth model and upper mouth model, each of which may include impressions of teeth, onto an articulator formed of a base member or bottom bow adapted to support the lower mouth model and a top member or top bow adapted to support the upper mouth model and wherein each of the base and top members has a layer of cured binding material formed thereon adjacent the respective mouth model and the detachable fastener comprises a first connecting means having an annular shaped connecting collar of a predetermined length and diameter which has extending axially from one side a spherical shaped joining member and extending axially from the other side an enlarged base member, and a second connecting means having a socket housing formed of an elongated, thin walled tubular member having an opening at one end thereof which extends into and through the interior of the socket housing wherein the opening is adapted to receive and pass the spherical shaped joining member into the interior of the socket housing and wherein the socket housing includes a means for defining in the interior wall of the thin walled tubular member adjacent the opening an annular shaped alignment and gripping member having a sloped edge which extends from the edge of the opening inwardly towards the interior of the socket housing such that when a spherical shaped joining member is inserted into the opening of the socket housing the spherical shaped joining member is directed into engagement with and past the alignment and gripping member until the sloping edge of the alignment and gripping member is positioned into removable gripping relationship with the spherical shaped joining member at approximately the location where it joins the connecting collar and wherein a separating force applied in a direction to urge the first connecting means away from the second connecting means results in the spherical shaped joining member abruptly overriding the gripping relationship of the alignment and gripping member thereagainst to permit separation of the spherical shaped joining member from the socket housing and removing of the mouth model from the articulator is shown. A method for fabricating apparatus for supporting impressions of a mouth on an articulator is shown.

12 Claims, 13 Drawing Figures

DETACHABLE FASTENER FOR JOINING IMPRESSIONS OF A MOUTH ONTO A DENTAL ARTICULATOR

BACKGROUND OF THE INVENTION

1. Field of the Invention

This invention relates to a detachable fastening means for removably joining a first article to a second article and more specifically relates to a detachable fastener for joining impressions of a mouth formed of a lower mouth model and an upper mouth model onto a dental articulator. The detachable fastener is adapted to respond to a separating force to enable the mouth models to be removably separated from their adjacent support member forming a part of the dental articulator.

2. Description of the Prior Art

It is well known in the art to utilize apparatus for supporting impressions of mouths including teeth wherein the impressions comprise a lower mouth model and an upper mouth model. The mouth models are adapted to be positioned in a contiguous relationship upon each other to provide centric, lateral and protrusive movements relative to each other. Typically, the lower mouth model and upper mouth model are supported by a dental articulator horizontal base member and a horizontal top member, respectively.

Generally, impressions of a mouth can be categorized into three groups. The first group is where there is a complete absence of teeth which is referred to as either a toothless model or an edentulous model. The second group is where anchor teeth are missing requiring a removable partial denture and this is referred to as a partially edentulous model. The third group is where some teeth are missing but there are sufficient anchor teeth remaining for crowns and inlays and is referred to as a fixed bridge model.

The process of making an impression of a mouth and the fabrication of partial dentures, fixed bridges and crowns in a dental laboratory is a slow, multi-step process. Typically a dentist takes an impression of a patient's mouth and forms an original casting, which is normally fabricated in plaster of paris. The original casting is delicate and will not withstand the application of heat and absorbs a large quantity of moisture during fabrication of a more permanent type of impression. Accordingly, a wax model is made from the original casting and a refractory model is formed using an appropriate refractory material which is cast by a centrifuge technique. Thereafter, the cast refractory model is cured by placing the same in boiling water. The cast refractory model is then attached to a layer of binding material formed on the dental articulator by use of a material known as dry lute with sticky wax.

In order to register either the upper or lower mouth model to the articulator and to obtain the desired alignment or occlusion between the upper and lower mouth models, keying grooves are cut in each mouth model in the bottom surfaces, opposite the mouth impressions. The keying grooves are lubricated with a separating media, such as for example soap, and placed onto a curable binding material, such as for example, soft plaster of paris.

As the curable binding material is cured and the mouth models dry, shrinkage occurs therebetween which results in slight errors being introduced into the occlusion between the upper and lower mouth models.

After the curable binding material is cured and is hard, the mouth models are removable from the binding material because of the presence of the separation media. In the fabrication of partial dentures, bridges and crowns, the mouth models must be removed from the dental articulator many times. A "sticky wax", formed of rosin, bees wax and other waxes, may be applied to the keyed grooves to act as an adhesive or intermediate binding material to hold the mouth models in place on the dental articulator.

Accordingly, many devices have been developed to permit removable attachment of the mouth model to a dental articulator.

One known technique is to attach a metal plate to the mouth model and use a removable pin which passes through a hole in the plate and the dental articulator to attach the mouth model to the dental articulator. Magnetic fastening devices are known wherein a magnetic field is utilized to clamp the mouth model to a dental articulator. Other known means for attachably supporting dental models to a dental articulator are disclosed in U.S. Pat. Nos. 2,765,533; 2,608,762; and 2,571,280.

In the fastening means adapted for use with a dental articulator disclosed in the above referenced Patents, a single ball and joint arrangement is utilized wherein a clamping plate or the like is joined to a surface of an upper mouth model or lower mouth model. The clamping plate includes means for forming one part of the ball and socket joint. A support arm, which forms the dental articulator, includes the other part of the ball and socket joint.

In each of the means for attaching the mouth models to the dental articulator disclosed in the above referenced U.S. Patents, the articulators are constructed to have a single ball and socket joint as a supporting means for the entire dental model and plaster base to be supported thereby. The size of the ball and socket joint is relatively large in order to support the entire weight of the mouth models and to align the mouth models relative to each other on the dental articulator itself.

In the dental articulators of U.S. Pat. Nos. 2,765,533 and 2,608,762, the support plates are affixed or attached to the mouth models by means of fasteners or adhesive. The dental articulator disclosed in U.S. Pat. No. 2,571,280 is attached to the dental articulator base through a binding layer of plaster of paris.

U.S. Pat. No. 3,694,919 discloses another form of a dental articulator which utilizes a pair of spherical styluses supported above lateral truss portions and above a vertically extending shank extending from the base of the articuator. The spherical styluses and truss portions form a pivotable support point between an upper member of the dental articulator which supports an upper mouth model and a vertically extended support which extends from the horizontal base member which is adapted to support the lower mouth model. In essence, the spherical styluses cooperate with a spherical stylus receiving socket within the lateral truss portion to permit relative movement of the horizontal top member of the dental articulator relative to the horizontal bottom member of the the dental articulator. Mouth models are affixed to the dental articulator by means of a screw which extends from the horizontal base member of the dental articulator into an aligned threaded aperture formed into the lower adjacent surface of the dental model. The mouth model is removably attached to the lower or base member of the dental articulator through the threaded connection.

The use of ball and socket joints as a fastening means for various other applications is well known in the art. Typical of such other applications are those disclosed in U.S. Pat. Nos. 4,044,725; 2,791,454 and 2,717,792, all of which disclose various embodiments of a spherical member and a cooperating socket member to form various types of ball and socket joints.

SUMMARY OF THE INVENTION

The present invention discloses a novel and unique detachable fastener for joining impressions of a mouth formed of a lower mouth model and an upper mouth model onto a dental articulator. By use of the detachable fastener of the present invention, an upper mouth model or lower mouth model can be easily affixed to or removed from a base member or a top member, respectively, of a dental articulator. The dental articulator has a layer of cured binding material formed thereon which is adjacent its respective mouth model and the layer of cured binding material is adapted to cooperate with the lower surface of its adjacent respective mouth model such that the detachable fastener is mounted therebetween. The detachable fastener, in the preferred embodiment, comprises a first connecting means having an annular shaped connecting collar having a predetermined axial length and a predetermined diameter, a spherical shaped joining member extending axially from one side of the connecting collar and an enlarged base member extending axially from the other side of the connecting collar.

The detachable fastener includes a second connecting means having a socket housing formed of an elongated, thin walled tubular member and having an aperture defining an opening at one end thereof which extends into the interior of the socket housing. The socket housing has an interior dimension which is adapted to receive and pass the spherical shaped joining member and the connecting collar. The socket housing includes means for defining an annular shaped alignment and gripping member located in the interior wall of the thin walled tubular member and positioned at the end of the socket housing adjacent the opening. The alignment and gripping member has a sloped edge which extends from the edge of the opening inwardly toward the interior of the socket housing a distance substantially equal to the axial length of the connecting collar.

The socket housing is adapted to have the spherical shaped joining member and connecting collar inserted into the opening wherein the spherical shaped joining member is directed into engagement with and past the alignment and gripping member until the sloping edge of the alignment and gripping member is positioned into removable gripping relationship with the spherical shaped joining member. When the first connecting means is in connecting or inserted relationship with the second connecting means, a separating force applied in a direction to urge the first connecting means away from the second connecting means results in the spherical shaped joining member abruptly overriding the gripping relationship to permit separation of the spherical shaped joining member from the socket housing.

The detachable fastener of the present invention overcomes several of the disadvantages of the known prior art to permit numerous attachment and removal of mouth models from a dental articulator. In addition, the detachable fastener of the present invention overcomes several of the disadvantages of the known prior art means for joining a first article to a second article.

In the known prior art devices, the means for connecting or fastening mouth models to dental articulators, utilize base plates, clamps, or screws requiring threaded apertures in the mouth models and adhesives. The known connecting fastening means are utilized to temporarily or permanently removably join an upper mouth model and a lower mouth model to a top member and bottom member, respectively, of a dental articulator. In the prior art devices which utilize base plates and clamping tabs, it is necessary to unbend tabs or to otherwise forceably remove a mouth model from a base plate, binding layer or supporting truss of a dental articulator in order to separate the same.

In a broader sense, the detachable fastener of the present invention can be utilized in a number of applications wherein it is desirable to utilize a detachable fastening to join a first article to a second article wherein a tight snug connection is desired. When the articles are held together and it is desirable to separate the same, the articles can be easily separated by application of a separation force therebetween to override the gripping relationship and permit separation of the spherical shaped joining member and connecting collar from the socket housing.

One advantage of the present invention is that standard dental articulators having horizontal base members and horizontal top members can be utilized using the known materials to form the layer of curable or cured binding materials. The present invention teaches inserting detachable fastening means into a layer of curable or cured binding material and into the outer bottom surface of an adjacent mouth model. In this manner, a detachable fastening relationship occurs between the layer of binding material and the lower surface of a mouth model such that the mouth model is held in a tight snug relationship against the layer of binding material when in an installed position. A user can easily remove a mouth model from a dental articulator by applying a small separation force between the articulator and the mouth model.

Yet another advantage of the present invention is that the mouth models can be easily installed and removed from a dental articulator independent of whether the mouth model is wet or dry.

Yet another advantage of the present invention is that three detachable fasteners can be positioned in a layer of curable or cured binding material at three points in a triangular relationship which are adapted to cooperate with three coaligned socket housings located in a similar arrangement on the outer bottom surface of an adjacent mouth model. Thus, during installation and removal of a mouth model from the dental articulator, a mouth model will always realign and seat itself in exactly the same position each time it is remounted thereby assuring that proper alignment will be obtained each time.

A still yet further advantage of the present invention is that during the fabrication process of the mouth models during the casting and related steps, a detachable fastening means in an assembled condition is positioned or located within the outer bottom surface of the mouth model with the socket housing member secured to the mouth model. After the mouth model with the assembled detachable fastening means is positioned on a layer of curable binding material while the binding material is in a pliable state, the enlarged base of the first connecting means is inserted into and embedded within the layer of pliable binding material. Upon hardening or curing of the layer of pliable binding material, a mouth model having the socket housing portion attached thereto, can be easily separated from the then embedded first connecting means within the layer of cured binding material.

A yet further advantage of the present invention is that the detachable fastening means can be fabricated from relatively inexpensive material and is, therefore, easy and economical to manufacture.

A still yet further advantage of the present invention is that the detachable fastening means can be deemed a consumable item and can be left within the mouth models.

A still yet further advantage of the present invention is that the apparatus can be fabricated for supporting impressions of a mouth which comprise a lower mouth model, an upper mouth model, and a dental articulator having horizontal base member and a horizontal top member, layers of cured binding material and a plurality of detachable fastening means each of which includes a spherical shaped joining member and a socket member. The apparatus so formed enables the mouth models to be removably attached to the dental articulator through detachable fastening means such that an application of a separating force between the articulator and the mouth models will result in the separating force overriding the gripping relationship of detachable fastening means to permit easy removal of the mouth models. In addition, the mouth model can be easily reinstalled or attached to the dental articulator by positioning each of the socket housings relative to its aligned opposed spherical shaped joining member secured in the layer of cured binding material and then by applying a small clamping force to the spherical shaped joining member. This results in the spherical shaped joining member being inserted into and through the socket housing into a gripping relationship with the alignment and gripping member.

BRIEF DESCRIPTION OF THE DRAWING

These and other objects and advantages of the invention, together with its various features and advantages, can be more easily understood from the following more detailed description of the preferred embodiment taken in conjunction with the accompanying drawing in which.

DESCRIPTION OF THE PREFERRED EMBODIMENT

Figure 1:
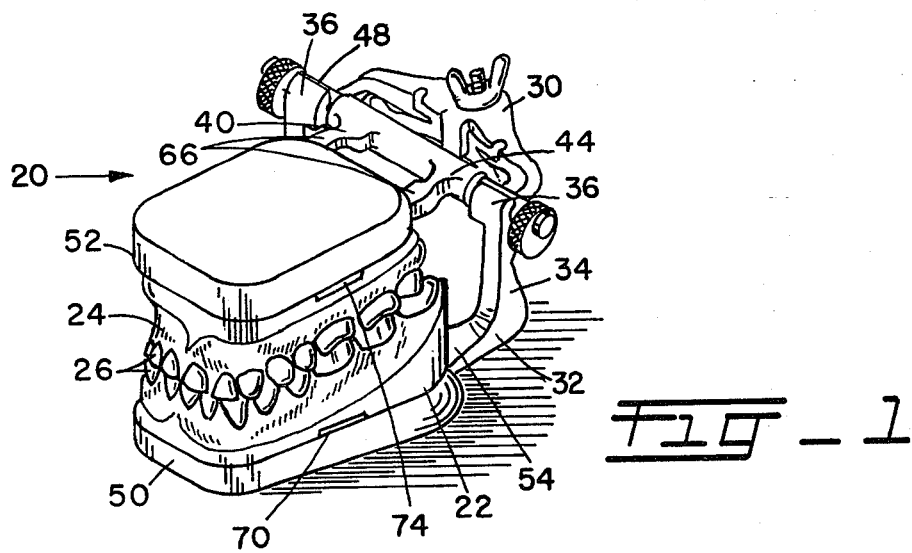
FIG. 1 is a perspective view of an apparatus for supporting impressions of a mouth having teeth which utilize detachable fastening means of the present invention.

FIG. 1 illustrates apparatus, shown generally by arrow 20, for supporting impressions of a mouth which comprise a lower mouth model 22 and an upper mouth model 24 positioned in a contiguous relationship upon each other to provide centric lateral, and protrusive movements relative to each other. In this embodiment, each of the mouth models 22 and 24 have impressions of teeth 26 formed therein. The apparatus further includes a dental articulator, shown generally as 30, having a horizontal base member 32 positioned adjacent the lower mouth model 22. The horizontal base member 32 includes a vertical upwardly extending bracket 34 having a support end 36 which is located a selected distance from the horizontal base member 32. The selected distance is that distance that is required to permit a lower mouth model and an upper mouth model to be positioned in the required contiguous relationship and to permit movement relative to each other as defined herein.

The dental articulator 30 further includes a horizontal top member 40 which is positioned adjacent the upper mouth model 24. The horizontal top member 40 includes a substantially outwardly extending support 44 which is pivotally and laterally supported by support end 36 of the vertical upwardly extending bracket 34 of the horizontal base member 32. The outwardly extending support 44 is pivotally supported with a support end 36 to permit rotation of the horizontal top member 44 toward and away from the horizontal base member 32 to provide for centric, lateral and protrusive movements of the mouth models 22 and 24 relative to each other.

In the known dental articulators, the vertical upwardly extending bracket 34 has a support end 36 which is annular in shape and has a hollowed out central area to act as a sleeve bearing. One edge of each of the support ends 36, generally shown as 48, is open and has a sufficient dimension to removably receive the outwardly extending support bracket 44 of the horizontal top member 40.

In addition, the known dental articulator's horizontal base member 32 and horizontal top member 34 each comprise elongated finger like members or tines which are adapted to cooperate with a pair of layers of rigid binding materials shown generally as 50 and 52.

In FIG. 1, the horizontal base member 32 has a pair of tines, shown as 54, which extend therefrom and cooperate with the layer of cured binding material 52.

The layer of cured binding material 50 is positioned between the horizontal base member 32, encloses tines 54 thereof and is contiguous the lower surface of the lower mouth model 22. Similarly, the horizontal top member 44, through its pair of tines 66 which are enclosed by the layer of cured binding material 52, is contiguous the outer bottom surface of upper mouth model 24.

A small recessed indentation 70 is provided in the surface of the lower mouth model 22 to permit a user to apply a separation force between the lower mouth model 22 and the combination layer of binding material 50 and horizontal base member 32. Application of a separating force between the mouth model 22 and the horizontal base member 32 results in the overriding of the gripping relationship of the detachable fasteners located between the lower surface of the lower mouth model 22 and the layer of rigid binding material 50 to permit separation thereof.

A similar indentation 74 is provided between the outer surface of the upper mouth model 24 and the layer of cured binding material 52.

Figures 2, 3:
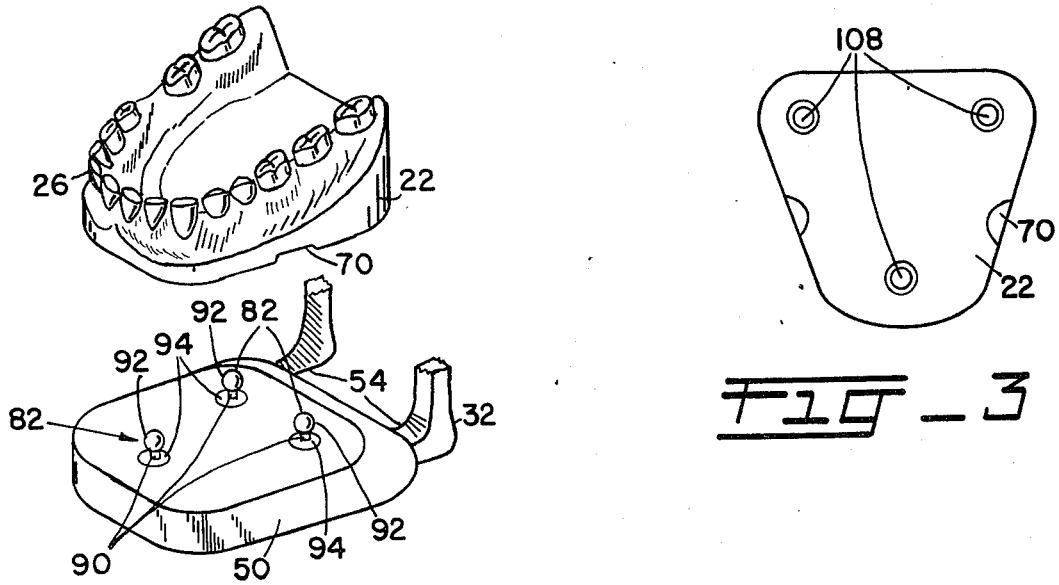
FIG. 2 is a perspective view of a lower mouth model, horizontal base member of a dental articulator and a layer of cured binding material formed on the lower base of the dental articulator and having a plurality of first connecting means extending therefrom.
FIG. 3 is a bottom plan view of an outer surface of a lower mouth model showing a socket housing.

FIG. 2 shows a lower mouth model 22 which has been separated from the horizontal base member 32 of the dental articulator 20. As shown in FIG. 2, the lower mouth model 22 has an indentation 70 formed on the outer bottom surface thereof. As shown in FIG. 2, the horizontal base member 32 has a pair of parallel tines 54 which extend into and are integral with the layer of cured binding material 50. In a typical dental laboratory, the layer of cured binding material comprises plaster of paris which has set. In practicing this invention, any known hardenable or curable pliable material may be used if the structural integrity thereof will hold and support a detachable fastener when hardened or cured.

When the layer of cured binding material 50 is applied onto the tines 54 of the horizontal base member 32, it is in a pliable or putty-like state. The layer of pliable, curable binding material is formed on the tines and has the top surface thereof somewhat leveled off.

The lower mouth model 22 has the second connecting means or socket housing portion of the detachable fasteners, such as shown as socket housings 108 in FIG. 3, embedded in the bottom outer surface of the lower mouth model 22. The unattached spherical shaped joining member and connecting collar are then inserted into the socket housing 108. The lower mouth model 22 having the assembled detachable fasteners is then positioned over and urged into mating relationship with the layer of pliable curable binding material 50. The second connecting means portion of the detachable fasteners are driven into and become embedded within the layer of pliable, curable binding material 50. When the layer of pliable, curable binding material 50 cures or hardens, the second connecting means becomes embedded therein such that the embedded second connecting means is capable of being retained in place by the layer of cured binding material 50. Application of a separating force applied between the lower mouth model 22 and the horizontal base member 32 enables separation and removal of the second connecting means embedded within the outer bottom surface of the lower mouth model 22 from the first connecting means embedded within the layer of cured binding material 50.

In FIG. 2, the first connecting means are shown generally as 82. In FIG. 2, a plurality of first connecting means 32 are arranged in a triangular pattern at the points of a triangle. The first connecting means 82 includes annular shaped connecting collar 90 having a predetermined axial length and predetermined diameter. A spherical shaped joining member 92 extends axially from one side of the connecting collar 90. In this embodiment, the diameter of the spherical shaped joining member 92 is greater than the diameter of the connecting collar 90. In addition, the first connecting means 92 has an enlarged base member, such as base member 94 illustrated in FIG. 9, which extends axially from the other side of the connecting collar 90. The enlarged base member 98 is embedded within the layer of cured rigid binding material 50.

Figures 4, 5:
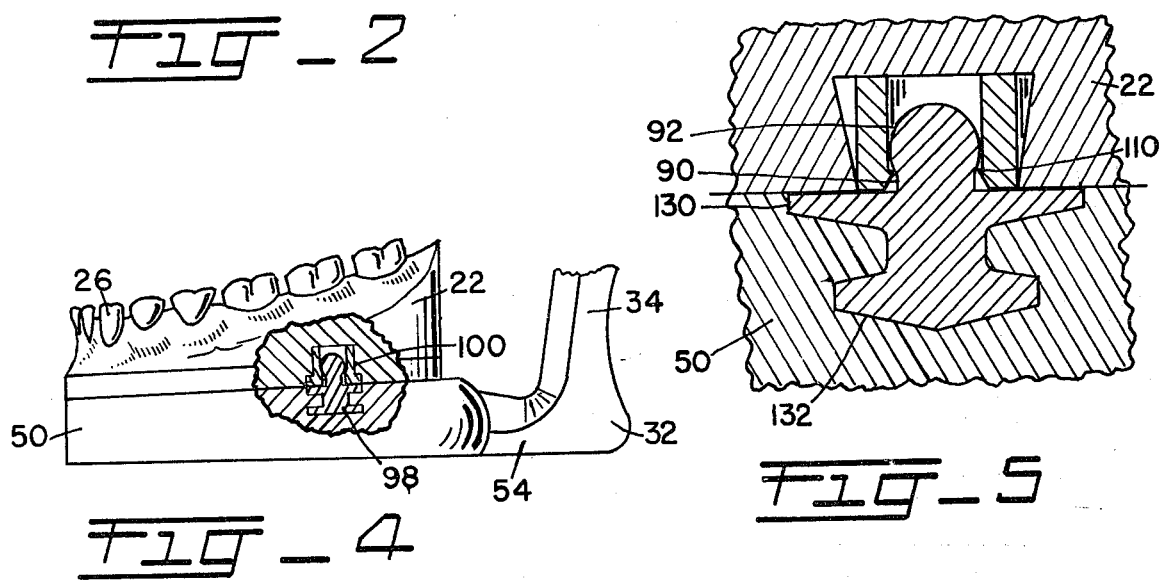
FIG. 4 is a partial plan view of a lower mouth model, horizontal base member and layer of cured binding material with one embodiment of a detachable fastening means shown partially in cross section in a gripping relationship.
FIG. 5 is a partial plan view showing, partially in cross section, another embodiment of a detachable fastening means.

FIG. 4 illustrates one embodiment of a detachable fastening means which includes a first connecting means and a second connecting means for joining a lower mouth model 22 to a layer of cured binding material 50. As shown in FIG. 4, the lower mouth model 22 includes impression of teeth 26 on one surface thereof and includes a second connecting means 100 which forms part of the detachable fastening means. The first connecting means 98 is embedded within the layer of cured binding material 50 which is supported by tines 54 of the horizontal base member 32 of the dental articulator.

In FIG. 4, the detachable fastening means includes a spherical shaped joining member which forms part of the first connecting means 98 and a socket member which forms part of the second connecting means 100. As illustrated in FIG. 4, the first connecting means 98 is adapted to receive and receives the second connecting means 100 in an overridable gripping relationship. The detachable fastening means is formed with one of the first connecting means 100 and second connecting means 100 in pairs, and which are embedded in cured binding materials 50, illustrated in FIG. 4, or 52 for the upper mouth model 24 as illustrated in FIG. 1, as the case may be.

The appropriate connecting means are located in the adjacent outer bottom surface of the appropriate mouth model in a cooperating relationship such that a first connecting means 98 is positioned in an opposed aligned relationship to the second connecting means 100. The detachable fastening means removably fastens and holds the lower mouth model and upper mouth model in position contiguous its respective rigid binding layer such that the lower mouth model 22 and the upper mouth model 24 are removable from the respective horizontal base member 32 and horizontal top member 40.

As illustrated in FIG. 4, the second connecting means 100 is located within the outer bottom surface of the lower mouth model 22 while the first connecting means 98 is located within the layer of cured binding material 50. However, it is envisioned that the position of each of the first connecting means and second connecting means could be reversed; that is, the first connecting means 98 could be located in the outer bottom surface of the lower mouth model 22 and the second connecting means 100 could be embedded within the layer of cured binding material 50.

Also as illustrated in FIGS. 2 and 3, a plurality of detachable fastening means can be used. In the preferred embodiment a set of three detachable fastening means is preferred. By positioning the same in a triangular pattern, proper alignment and seating can be obtained between the mouth models and the respective layers of cured binding material.

Figure 8:
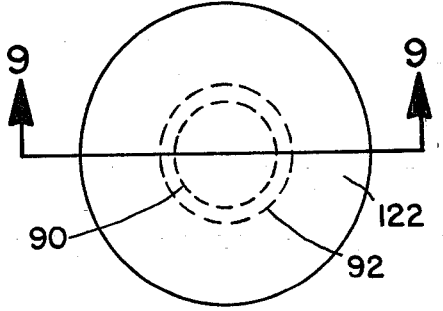
FIG. 8 is a top plan view of a first connecting means having two opposed coplanar enlarged base members extending therefrom.
Figure 9:
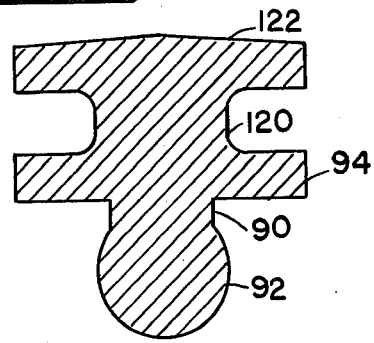
FIG. 9 is a sectional view of a first connecting means having a spherical shaped joining member taken along section lines 9—9 of FIG. 8.

In FIG. 4, one embodiment of a detachable fastening means is illustrated wherein the first connecting means includes an enlarged base which is formed of a pair of spaced parallel members which are illustrated in greater detail in FIGS. 8 and 9. Similarly, the second connecting means which includes a socket housing, includes a protruding anchoring lip which extends around the periphery thereof as illustrated in greater detail in FIGS. 6 and 7.

FIG. 5 illustrates another embodiment of a detachable fastener for joining impressions of teeth to a dental articulator. FIG. 5 illustrates pictorially a second embodiment of a detachable fastening means joining an impression of a mouth formed of lower mouth model 22 to a layer of cured binding material 50. The detachable fastening means formed of a first connecting means and a second connecting means which are in a gripping relationship. The first connecting means includes an annular shaped connecting collar 90 having a predetermined axial length and a predetermined diameter. A spherical shaped joining member 92 extends axially from one side of the connecting collar 90 and in this embodiment has a diameter which is greater than the diameter of the connecting collar 90. An enlarged base member 130 extends axially from the other side of the connecting collar 90. The base member 130 in the preferred embodiment is annular shaped and has a geometrical dimension which is greater than the diameter of the annular shaped connecting collar. In addition, a second enlarged base member which is also annular shaped having a smaller diameter than base member 130, functions as an anchoring tab 132. This second enlarged base 132 likewise extends axially from the enlarged base member 130 to insure embedding of the first connecting means within the layer of cured binding material 50.

Figure 7:
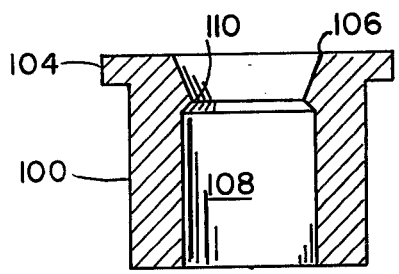
FIG. 7 is a sectional view of the socket housing taken along section lines 7—7 of FIG. 6.

The second connecting means has a socket housing which is formed of a thin walled tubular member having an aperture which defines an opening at one end thereof and which extends in the interior of the socket housing which is illustrated in greater detail in FIG. 7. The socket housing has an interior predetermined dimension which is at least equal to the sum of the diameter of the spherically shaped joining member 92 and the axial length of the connecting collar 90. The socket housing includes means for defining an annular shaped alignment and gripping member 110 located in the interior wall of the thin walled tubular member and positioned at the end of the socket housing adjacent the opening.

Figure 6:
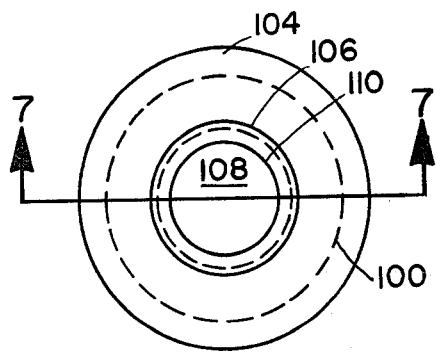
FIG. 6 is a top plan view of a second connecting means of the detachable fastener having a protruding anchoring lip around the opening thereof and vertically extending exterior walls.

FIGS. 6 and 7 show the details of a second connecting means comprising a socket housing 100 having an aperture which extends from one end thereof through the interior 108 of the socket housing 100 a distance which is substantially equal to the geometrical dimension of the axial length of the connecting collar 90. The socket housing 100 includes a protrusion anchoring lip 104 extending around the periphery thereof near the opening 106.

The socket housing 100 includes means for defining an annular shaped alignment and gripping member 110 which is located in the interior wall of the opening 108 formed in the socket housing 100. The alignment and gripping member 110 is positioned at the end of the socket housing 100 adjacent the opening 106. The alignment and gripping member 110 has a sloped edge which extends from the edge of the opening 106 inwardly toward the interior 108 of the socket housing 100, a distance substantially equal to the axial length of the connecting collar 90. The socket housing 100 is adapted to have the spherical shaped joining member 92 and the connecting collar 90 inserted into the opening 106. The so inserted spherical shaped joining member 92 is directed into engagement with and past the alignment and gripping member 110 until the sloping edge thereof is positioned into removable or overridable gripping relationship with the spherical shaped joining member 92 and connecting collar 90. In the assembled or gripping arrangement, a separating force applied to the indentation 70 and in a direction to urge the first connecting means away from the second connecting means results in the spherical shaped joining member 92 abruptly overriding the gripping relationship of the alignment and gripping member 110 and the spherical shaped joining member 92 separating from the socket housing 100 to enable the mouth model 22 to be separated from the layer of cured binding material 50.

In FIG. 9, the first connecting means illustrated therein includes a pair of spaced parallel annular shaped members 94 and 122 which provide means for embedding the first connecting means within the layer of cured binding material. An opening or groove 120 is formed between the annular shaped members 94 and 122 to permit anchoring the first connecting means within the layer of cured binding material 50. FIG. 8 illustrates the geometrical relationship between the diameter of the connecting collar 90 and the diameter of the spherical shaped connecting member 92, it being noted that the diameter of the spherical shaped connecting member 92 is substantially the same as the diameter of the groove 120 located between the spherical shaped annular members 94 and 122. As illustrated in FIG. 9, the second annular shaped member 122 has a slightly inclined peak formed therein to essentially form an anchoring tab to embed the first connecting means within the layer of cured binding material.

Figure 10:
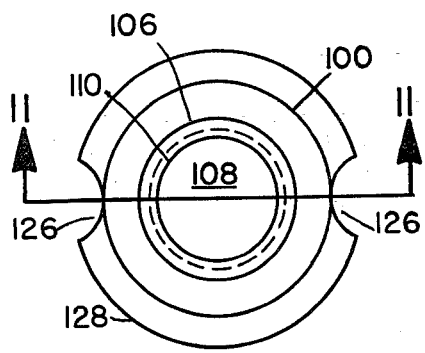
FIG. 10 is a top plan view of another embodiment of a detachable fastening means having outwardly sloping external walls and a pair of opposed parallel grooves formed on the exterior thereof.
Figure 11:
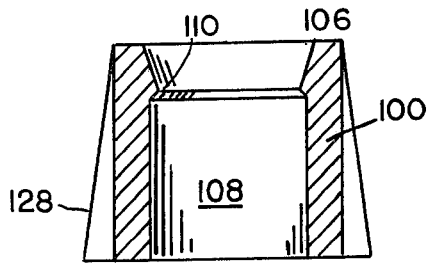
FIG. 11 is a sectional view of a second connecting means taken along section lines 11—11 of FIG. 8.

FIGS. 10 and 11 illustrate in greater detail a second embodiment of the detachable fastening means illustrated in FIG. 5. In FIG. 10, the alignment and gripping member 110, the opening 106 and the interior 108 formed by the aperture extending through the thin walled socket housing 100 are illustrated. The exterior walls of the socket housing 100 are outwardly sloping in shape forming flaired walls 128 in order to provide secure anchoring of the second connecting means within the outer bottom surface of a mouth model. As illustrated in FIG. 10, a pair of spaced parallel axially aligned slots 126 are formed within the flaired walls 128 of the socket housing 100 in order to provide additional surface area for embedding the socket housing 100 and the mouth model.

Figure 12:
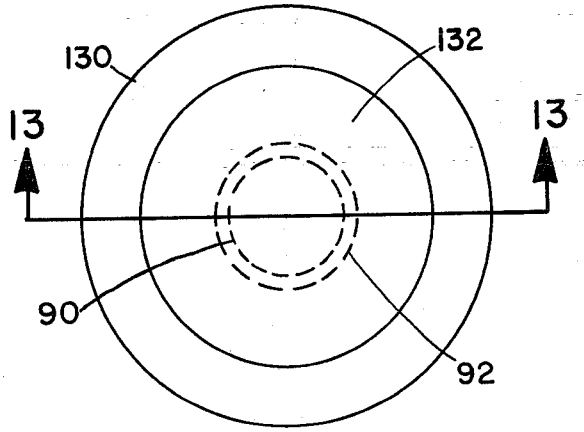
FIG. 12 is a top plan view of a first connecting means having a spherical shaped joining member which is adapted to cooperate with and be received by the socket housing illustrated in FIG. 10.
Figure 13:
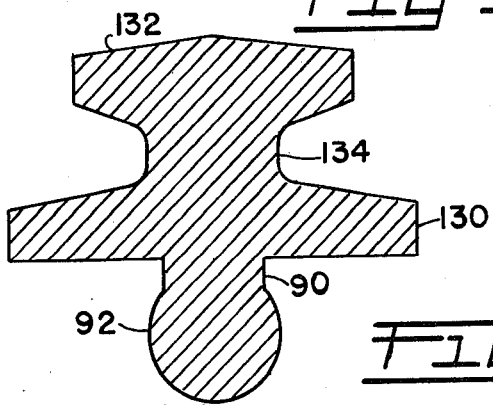
FIG. 13 is a sectional view of the first connecting means taken along section lines 12—12 of FIG. 11.

FIGS. 12 and 13 illustrate another embodiment of a first connecting means. The connecting collar 90 and spherical shaped joining member 92 of the first connecting means are similar to those of FIG. 9. However, the enlarged base is formed of a first annular shaped member 130 and a second smaller annular shaped member 132 which is spaced from the first annular shaped member 130. The annular shaped members 130 and 132 are separated by a shaped groove 134 which functions to embed the first connecting means within the layer of cured binding material adjacent the appropriate horizontal base member or horizontal top member of a dental articulator.

The top plan view of the first connecting means illustrated in FIG. 12 shows the relationship between the diameter of the connecting collar 90 and the diameter of the spherical shaped joining member 92. In this embodiment this diameter of the spherically shaped joining member 92 is substantially equal to that of the groove 134 formed therein.

The embodiments illustrated in FIGS. 10 through 13, inclusive, are adapted to be formed by using well known tool and die molds in order to fabricate the detachable fastener in high production.

In the preferred embodiment, the detachable fastener was formed of cement gypsum, type 212 at 50 PSI using injection molding. In the embodiment illustrated in FIGS. 10 through 13, the overall diameter of the opening of the housing was in the order of 0.300 inches and the depth thereof 0.280 inches. The downwardly sloping angle of the alignment and gripping member was approximately 20° from the vertical and the undercut at the end of the downwardly sloping walls was approximately 45° from the vertical. In addition, the depth of the alignment and gripping member was approximately 0.064 inches. The diameter of the connecting collar was on the order of 0.140 inches and the axial length of the collar approximately 0.038 inches. The diameter of the spherical shaped joining member was about 0.188 inches. The dimensions of the spherical shaped joining member and the connecting collar are adjusted or varied so that the spherical shaped joining member and connecting collar will have a "snap together" fit with the socket housing.

By using the teachings of the present invention, a new and novel process for fabricating apparatus for supporting impressions of a mouth can be fabricated.

The method for fabricating apparatus for supporting impressions of a mouth on a dental articulator comprises the steps of securing at least one of a first connecting means and a second connecting means in the outer bottom surface of a mouth model adapted to be mounted on a horizontal base member of a dental articulator; inserting the other of the first connecting means and second connecting means in a gripping relationship with the connecting means already embedded in the outer bottom surface of said mouth model; forming on a selected part of a dental articulator a layer of curable pliable binding material which is capable of being hardened or cured; positioning the mouth model having the detachable fastening means inserted therein into contiguous relationship with the layer of curable pliable binding material and urging the mouth model into intimate contact therewith to embed the unsecured connecting means mated with and extending from the outer bottom surface of the mouth model within the layer of curable pliable binding material; and hardening or curing the layer of pliable binding material to form a relatively rigid structure between the dental articulator and the embedded connecting means.

The additional steps of applying a separating force between the mouth model and layer of cured binding material to cause an overriding gripping relationship between the first connecting means and the second connecting means to permit separation of the mouth model from the layer of cured binding material may be performed.

The present invention has utility in the dental field for fabrication of impressions of mouth models. In the preferred embodiment, the socket housing member is embedded within the outer bottom surface of the mouth model in order to provide a flat substantially planar surface such that the mouth model can be placed upon a flat surface for working with or on the same. However, in some applications it may be desirable to have the spherical shaped joining members mounted in the outer bottom surface of the mouth model and the socket housing within the layer of cured binding material.

There are numerous dental, medical, industrial, consumer and other applications where it is desirable to fasten a first article to a second article in a tight, snug relationship which can be easily separated by a separation force wherein the spherical shaped joining member overrides the gripping relationship of the alignment and gripping member within the socket housing to permit removal and separation of the detachable fastening means and of the articles which contained the connecting means.

The connecting means can be mounted or secured to or within the articles using any number of known techniques including, without limitation, adhesive, fasteners or the like.

In the preferred embodiment, a plurality of detachable fasteners are utilized in order to join a layer of cured binding material to mouth models. The preferred embodiment is a triangular shaped arrangement having three detachable fasteners arranged at the points of a triangle to provide maximum alignment and proper orientation of the mouth model to the layer of cured binding material each time the mouth model is reassembled upon a dental articulator. This is particularly true when it is desirable to provide for consistent and uniform centric, lateral and protrusive movements between the various mouth models.

If desired, any number of detachable fasteners may be used for joining the mouth models to a dental articulator with between two to four detachable fasteners being possible and three being preferable.

What is claimed is:

1. A detachable fastener for joining impressions of a mouth formed of a lower mouth model and upper mouth model onto a dental articulator having a base member which is adapted to support the lower mouth model and a top member which is adapted to support the upper mouth model and wherein each member has a layer of cured binding material formed thereon adjacent its respective mouth model, said detachable fastener comprising a first connecting means located in one of a said mouth model and a layer of cured binding material having an annular shaped connecting collar having a predetermined axial length and predetermined diameter, a spherical shaped joining member extending axially from one side of said connecting collar and having a diameter which is greater than the diameter of the connecting collar and an enlarged base member extending axially from the other side of said connecting collar, said base member having a geometrical dimension which is greater than the predetermined diameter of the annular shaped connecting collar; and a second connecting means located in the other of a said mouth model and a layer of cured binding material having a socket housing formed of an elongated, thin walled tubular member and having an opening at one end thereof which extends into the interior of the socket housing, said socket housing having an interior dimension which is at least equal to the sum of the diameter of said spherical shaped joining member and the axial length of the connecting collar, said socket housing including means for defining an annular shaped alignment and gripping member adjacent the opening, said alignment and gripping member having a sloped edge which extends from the edge of the opening inwardly toward the interior of the socket housing a distance substantially equal to the axial length of said connecting collar, said socket housing being adapted to have a said spherical shaped joining member and said connecting collar inserted into said opening wherein said spherical shaped joining member is directed into engagement with and past said alignment and gripping member until the sloped edge of the alignment and gripping member is positioned into a removable gripping relationship with the spherical shaped joining member and connecting collar wherein a separating force applied in a direction to urge said first connecting means away from said second connecting means results in the spherical shaped joining member abruptly overriding said gripping relationship to permit separation of the spherical shaped joining member and connecting collar from the socket housing.

2. The detachable fastener of claim 1 wherein said enlarged base member is a first annular shaped member which is located adjacent the connecting collar and said first connecting means includes
   a second annular shaped member which is spaced a predetermined distance from the first annular shaped member and has a groove formed therebetween to form an anchoring tab which is adapted to embed the first connecting means within one of a said dental model and a layer of rigid binding material.

3. The detachable fastener of claim 2 wherein said second annular shaped member has a geometrical dimension substantially equal to that of said first annular shaped member.

4. The detachable fastener of claim 2 wherein said second annular shaped member has a geometrical dimension which is less than that of said first annular shaped member.

5. The detachable fastener of claim 1 wherein said second connecting means includes a protruding anchoring lip formed around the periphery of the socket housing and located at the end thereof adjacent the opening.

6. The detachable fastener of claim 1 wherein said second connecting means includes an outwardly extending flared wall member and means defining a pair of spaced parallel axially aligned slots formed in the periphery thereof.

7. The detachable fastener of claim 1 wherein said first connecting means and second connecting means is formed of a gypsum type 121 material.

8. The detachable fastener of claim 1 wherein said first connecting means spherical shaped joining member has a diameter which is slightly greater than the diameter of said connecting collar.

9. The detachable fastener of claim 8 wherein the end of the socket housing opposite to said opening has a bottom opening.

10. Apparatus for supporting impressions of a mouth comprising
    a lower mouth model and an upper mouth model adapted to be positioned in a contiguous relationship upon each other to provide centric, lateral and protrusive movements relative to each other;
    a dental articulator having
       a horizontal base member positioned adjacent the lower mouth model, said horizontal base member including a vertical upwardly extending bracket having a support end which is located a selected distance from the horizontal base member; and
       a horizontal top member positioned adjacent the upper mouth model, said horizontal top member including a substantially outwardly extending support which is pivotally and laterally supported by the support end of the vertical upwardly extending bracket of said horizontal base member to permit rotation of said horizontal top member towards and away from said horizontal base member and to provide for centric, lateral and protrusive movements of the mouth models relative to each other;
    a pair of layers of cured binding material one of which is located between the horizontal base member and the lower mouth member and the other of which is located between the horizontal top member and the upper mouth member, each of said pair of layers of cured binding material being positioned contiguous its associated horizontal base member and horizontal top member; and
    a plurality of detachable fastening means each of which includes a spherical shaped joining member and socket housing wherein said socket housing is adapted to receive said spherical shaped joining member in an overridable gripping relationship, said detachable fastening means being mounted with one of said socket housings and said spherical shaped joining members in said pairs of layers of cured binding material and in adjacent surfaces of the lower mouth model and upper mouth model in a cooperating relationship such that one spherical shaped joining member is positioned in opposed aligned relationship to be inserted into and removed from a cooperating socket housing to removably fasten and hold the lower mouth model and upper mouth model in position contiguous its respective layer of cured binding material such that the lower mouth model and upper mouth model are removable from their respective horizontal base member and horizontal top member or the dental articulator.

11. A method for fabricating apparatus for supporting impressions of a mouth on a dental articulator comprising the steps of
    securing at least one of a first connecting means and a second connecting means in the outer bottom surface of a mouth model adapted to be mounted on a horizontal base member of a dental articulator;
    inserting the other of said first connecting means and second connecting member in a gripping relationship with the connecting means already embedded in the outer bottom surface of said mouth model;
    forming on a selected portion of a dental articulator a layer of curable, pliable binding material which is capable of becoming cured;
    positioning the mouth model having the detachable fastening means inserted therein into contiguous relationship with the layer of curable, pliable binding material and urging the mouth model into intimate contact therewith to embed the unsecured connecting means mated with and extending from the outer bottom surface of the mouth model within the layer of curable pliable binding material; and curing the layer of curable, pliable binding material to form a relatively rigid structure between the dental articulator and the embedded connecting means.

12. The method of claim 11 wherein said first connecting means has a spherical shaped joining member and connecting collar and said secured connecting means includes a socket housing having an alignment and gripping member which receives and passes the spherical shaped joining member to form a gripping relationship therebetween and further including the step of applying a separating force between the mouth model and layer of cured binding material to override the gripping relationship between the first connecting means and the second connecting means to permit separation of the mouth model from the layer of cured binding material.

* * * * *